United States Patent
Pazenok et al.

(10) Patent No.: US 8,222,435 B2
(45) Date of Patent: *Jul. 17, 2012

(54) DIOXOLANE AND DIOXANE DERIVATIVES AND A PROCESS FOR THEIR PREPARATION

(75) Inventors: Sergii Pazenok, Solingen (DE); Norbert Lui, Odenthal (DE); Igor Gerus, Kiew (UA); Olga Balabon, Kiew (UA)

(73) Assignee: Bayer CropScience AG, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/969,138

(22) Filed: Dec. 15, 2010

(65) Prior Publication Data

US 2011/0152531 A1 Jun. 23, 2011

(30) Foreign Application Priority Data

Dec. 15, 2009 (EP) .................... 09179298

(51) Int. Cl.
*C07D 319/12* (2006.01)
*C07D 307/00* (2006.01)
*C07D 317/00* (2006.01)
*C07D 323/02* (2006.01)

(52) U.S. Cl. ......... 549/377; 549/380; 549/430; 549/455

(58) Field of Classification Search .................. None
See application file for complete search history.

(56) References Cited

U.S. PATENT DOCUMENTS

| 2,556,135 | A | | 6/1951 | Croxall et al. |
|---|---|---|---|---|
| 5,064,944 | A | * | 11/1991 | Armstrong ................. 536/123.1 |
| 2009/0275471 | A1 | | 11/2009 | Funke et al. |
| 2010/0029478 | A1 | | 2/2010 | Alig et al. |
| 2011/0152532 | A1 | | 6/2011 | Pazenok et al. |

OTHER PUBLICATIONS

Cabiddu, S. et al., "Heterocyclic Compound Studies. II. Synthesis of 1,4-Benzodioxin, 1,4-Benzoxathiin, 1,4-Benzoxazine and 1,4-Benzothiazine Derivatives," *J. Heterocycl. Chem.* 23:1815-1820, Wiley, Hoboken, New Jersey (1986).

Fan, M.-J. et al., "DABCO catalyzed reaction of various nucleophiles with activated alkynes leading to the formation of alkenoic acid esters, 1,4-dioxane, morpholine, and piperazinone derivatives," *Tetrahedron* 62:6782-6791, Elsevier Ltd., Oxford, United Kingdom (2006).

Fukuda, H. et al., "Spontaneous Copolymerization of 4-Methylene-1,3-Dioxolanes with Maleic Anhydride," *J. Polym. Sci. A. Polym. Chem.* 20:1401-1409, John Wiley & Sons, Inc., New York, New York (1982).

Gevorkyan, A.A. et al., "Tetrafluoroboric Acid—A New Catalyst for the Synthesis of 1,3-Dioxolanes, Preparation of Hydroxyacetone," *Translated from Khimiya Geterotsiklicheskikh Soedinenii*, No. 1, pp. 33-36, Plenum Publishing Corporation (1991).

Kankaanperä, A. et al., "A Novel Route to 1,3-Dioxoles via a General Acid-Catalyzed Isomerization Reaction," *Acta Chem. Scand.* 20:2622-2623, Munksgaard International Publishers, Copenhagen, Denmark (1996).

Mattay, J. et al., "Synthese von substituierten 1,3-Dioxolen," *Sythesis* 3:208-210, Georg Thieme Verlag, Stuttgart, Germany (1983).

Pedduri, Y. and Williamson, J.S., "One-pot synthesis of highly substituted tetrahydrofurans from activated propargyl alcohols using Bu$_3$P," *Tetrahedron Lett.* 49:6009-6012, Elsevier Ltd., Oxford, United Kingdom (2008).

Rossi, A. and Schinz, H., "Sulla costituzione dei prodotti di condensazione del cloralio con etossalil-chetoni," *Helv. Chim. Acta* XXXII:1967-1974, Verlag Helvetica Chimica Acta, Basel, Switzerland (1949).

International Search Report for International Patent Appl. No. PCT/EP2010/069380, European Patent Office, The Netherlands, mailed Feb. 22, 2011.

* cited by examiner

*Primary Examiner* — Rita Desai
*Assistant Examiner* — Ben S Michelson
(74) *Attorney, Agent, or Firm* — Sterne, Kessler, Goldstein & Fox P.L.L.C.

(57) ABSTRACT

The present invention relates to novel acylmethylene-1,3-dioxolanes and acylmethylene-1,4-dioxanes of the general formula (I)

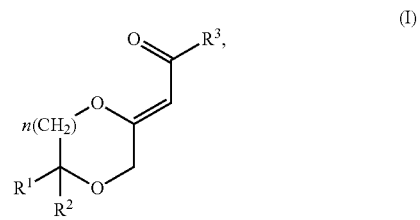

in which $R^1$, $R^2$, $R^3$ and n have the meanings given in the description, and also a novel process for their preparation. Acylmethylene-1,3-dioxolanes and acylmethylene-1,4-dioxanes are important intermediates for the preparation of pyrazoles and anthranilamides, which can be used as insecticides.

10 Claims, No Drawings

DIOXOLANE AND DIOXANE DERIVATIVES AND A PROCESS FOR THEIR PREPARATION

CROSS-REFERENCE TO RELATED APPLICATION

This application claims benefit to European Patent Application No. 09179298.6, filed Dec. 15, 2009.

BACKGROUND OF THE INVENTION

1. Field of the Invention

The present invention relates to novel acylmethylene-1,3-dioxolanes and acylmethylene-1,4-dioxanes, and to a novel process for their preparation.

Acylmethylene-1,3-dioxolanes and acylmethylene-1,4-dioxanes are important intermediates for the preparation of pyrazoles and anthranilamides, which can be used as insecticides.

2. Description of the Related Art

The literature has already described how certain dioxolane derivatives in the presence of acid anhydrides have a tendency towards spontaneous polymerization (*Spontaneous co-polymerization of 4-methylene-1,3-dioxolanes with maleic anhydride*, Fukuda, Hiroyuki; Hirota, Masahiro; Nakashima, Yoshihiro, Nagoya Munic. Ind. Res. Inst., Rokuban, Japan, Journal of Polymer Science, Polymer Chemistry Edition (1982), 20 (6), 1401-9.) The acylmethylene-1,3-dioxolanes and acylmethylene-1,4-dioxanes according to the invention, however, are not described; a process for their preparation is not described in the literature either.

It was therefore an object to provide a process which allows acylmethylene-1,3-dioxolanes and acylmethylene-1,4-dioxanes to be prepared in a simple manner without the disadvantages described in the prior art and on an industrial scale from known 4-methylene-1,3-dioxolanes and 6-methylene-1,4-dioxanes.

SUMMARY OF THE INVENTION

According to the invention, the object was achieved by a process for the preparation of novel acylmethylene-1,3-dioxolanes and acylmethylene-1,4-dioxanes of the formula (I),

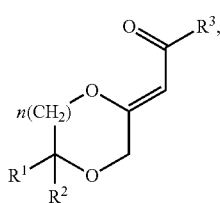

(I)

in which
$R^1$ and $R^2$, independently of one another, are hydrogen, alkyl, haloalkyl, aryl or alkylaryl,
$R^1$, $R^2$ further form a 4, 5, 6, or 7-membered saturated ring which is optionally substituted and which optionally contains 1 to 2 hetero atoms selected form N, S and O,
n is 0 or 1,
$R^3$ is $CX_3$, $(C=O)$Oalkyl or $(C=O)$Oaryl,
X is halogen, by reacting compounds of the formula (II),

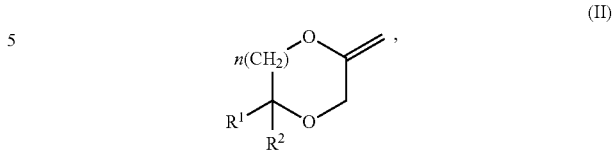

(II)

in which
$R^1$, $R^2$ and n have the meanings given above,
with compounds of the general formula (III), for example acid chlorides or anhydrides,

(III)

in which
$R^3$ and X have the meanings given above and
$R^4$ is X, $O(C=O)R^3$ or $(CH_3)_3COO$,
to give acylmethylene-1,3-dioxolanes and acylmethylene-1,4-dioxanes according to the invention of the general formula (I).

It is regarded as surprising that by virtue of the process according to the invention it is possible to prepare the novel acylmethylene-1,3-dioxolanes and acylmethylene-1,4-dioxanes of the formula (I) selectively and in a high yield without observing troublesome secondary reactions.

Examples of compounds of the formula (I) that can be prepared by the process according to the invention are: 1,1,1-Trichloro-3-(2,2-dimethyl-1,3-dioxolan-4-ylidene) acetone, methyl 3-(2,2-dimethyl-1,3-dioxolan-4-ylidene)-2-oxopropanoate, methyl 3-(1,3-dioxolan-4-ylidene)-2-oxopropanoate, ethyl 3-(2,2-dimethyl-1,3-dioxolan-4-ylidene)-2-oxopropanoate, ethyl 3-(5,5-dimethyl-1,4-dioxan-2-ylidene)-2-oxopropanoate.

DETAILED DESCRIPTION OF THE INVENTION

General Definitions

In connection with the present invention, the term halogens (X) includes, unless defined otherwise, those elements selected from the group consisting of fluorine, chlorine, bromine and iodine, where fluorine, chlorine and bromine are preferably used and fluorine and chlorine are particularly preferably used. Substituted groups can be mono- or polysubstituted, where, in the case of multiple substitutions, the substituents may be identical or different.

Alkyl groups substituted with one or more halogen atoms (—X)=(haloalkyl groups) are selected, for example, from trifluoromethyl ($CF_3$), difluoromethyl ($CHF_2$), $CCl_3$, $CFCl_2$, $CF_3CH_2$, $ClCH_2$, $CF_3CCl_2$.

In connection with the present invention, unless defined otherwise, alkyl groups are linear or branched hydrocarbon groups.

The definition alkyl and $C_1$-$C_{12}$ alkyl includes, for example, the meanings methyl, ethyl, n-propyl, isopropyl, n-butyl, isobutyl, sec-butyl and t-butyl, n-pentyl, n-hexyl, 1,3-dimethylbutyl, 3,3-dimethylbutyl, n-heptyl, n-nonyl, n-decyl, n-undecyl, n-dodecyl.

In connection with the present invention, unless defined otherwise, cycloalkyl groups are ring-shaped saturated hydrocarbon groups.

In connection with the present invention, unless defined otherwise, aryl radicals are aromatic hydrocarbon radicals which can have one, two or more heteroatoms selected from O, N, P and S and may be optionally substituted by further groups.

In connection with the present invention, unless defined otherwise, alkylaryl groups are alkyl-group-substituted aryl groups which can have a $C_{1-8}$-alkylene chain and can have one or more heteroatoms selected from O, N, P and S in the aryl backbone.

The compounds according to the invention can, if appropriate, be present as mixtures of different possible isomeric forms, in particular stereoisomers, such as e.g. E- and Z-, threo- and erythro-, and also optical isomers, but optionally also tautomers. Both the E- and the Z-isomers, as well as the threo- and erythro-, and also the optical isomers, any desired mixtures of these isomers, and the possible tautomeric forms are disclosed and claimed.

4-Methylene-1,3-dioxolane and 6-methylene-1,4-dioxane Derivatives of the Formula (II)

The 4-methylene-1,3-dioxolanes and 6-methylene-1,4-dioxanes used as starting materials for carrying out the process according to the invention are generally defined by the formula (II),

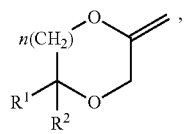

(II)

where
$R^1$ and $R^2$, independently of one another, are hydrogen, alkyl, haloalkyl, aryl or alkylaryl,
$R^1$, $R^2$ further form a 4, 5, 6, or 7-membered saturated ring which is optionally substituted and which optionally contains 1 to 2 hetero atoms selected form N, S and O,
$R^1$ and $R^2$, independently of one another, are preferably hydrogen or $(C_1-C_{12})$-alkyl,
$R^1$ and $R^2$, independently of one another, are particularly preferably hydrogen or methyl,
n is 0 or 1, preferably and particularly preferably 0.

Examples of starting materials suitable according to the invention are 2,2-dimethyl-4-methylene-1,3-dioxolane, 4-methylene-1,3-dioxolane or 2,2-dimethyl-6-methylene-1,4-dioxane. The compounds are known and can be prepared as described in Gevorkyan, A. A. et al. Khimiya Geterotsiklicheskikh Soedinenii (1991), (1), 33-6;
as in J. Mattay et al Synthesis (1983), (3), 208-10;
or as in A. Kankaanpera et al., Acta Chemica Scandinavica (1966), 20 (9), 2622.

Compounds of the Formula (III)

The compounds used as starting materials for carrying out the process according to the invention are generally defined by the formula (III):

(III)

where
$R^3$ is $CX_3$, (C=O)Oalkyl or (C=O)Oaryl,
$R^3$ is preferably $CX_3$, (C=O)Oalkyl,
$R^3$ is particularly preferably (C=O)Oalkyl,
X is halogen,
X is preferably and particularly preferably chlorine,
$R^4$ is X, O(C=O)$R^3$ or $(CH_3)_3COO$,
$R^4$ is preferably X, particularly preferably chlorine.

Examples of compounds of the formula (III) which can be used in the process according to the invention are $CF_3COCl$, $CCl_3COCl$, $ClCOCOOMe$, $ClCOCOOEt$, $(CF_3CO)_2O$, $CCl_3COF$, $CF_2HCOOCOC(CH_3)_3$. The compounds are commercially available.

Reaction Procedure

The process step according to the invention is preferably carried out within a temperature range from −20° C. to 100° C., preferably −10° C. to 40° C., particularly preferably at temperatures of from 0° C. to 30° C. The process step according to the invention is generally carried out under atmospheric pressure.

The reaction time is not critical and can be selected in a range between 30 min and several hours depending on the batch size and the temperature.

When carrying out the process step according to the invention, 1 mol of the 4-methylene-1,3-dioxolane or 6-methylene-1,4-dioxane derivative of the formula (II) is reacted with 0.8 mol to 1.5 mol, preferably 0.9 mol to 1.2 mol, particularly preferably with the equimolar amount, of the compound of the formula (III).

The acylation is generally carried out in the presence of a base. Suitable bases are, for example, aliphatic, alicyclic, cyclic or aromatic tertiary amines such as: trimethylamine, triethylamine, tributylamine, methyldiisopropylamine, benzyldimethylamine, pyridine, 2-, 3- or 4-methylpyridine, 2,3-dimethylpyridine, 2-methyl-5-ethylpyridine, 2,6-dimethylpyridine, 2,5-dimethylpyridine, 2,4,6-trimethylpyridine, DBU, DABCO, N-methylmorpholine, dimethylcyclohexylamine. Inorganic bases are $NaHCO_3$, LiOH, NaOH, KOH, $Na_2CO_3$, $K_2CO_3$. Particular preference is given to using triethylamine, pyridine, benzyldimethylamine, dimethylpyridine, potash.

Suitable solvents are, for example, aliphatic, alicyclic or aromatic hydrocarbons, such as e.g. petroleum ether, n-hexane, n-heptane, cyclohexane, methylcyclohexane, benzene, toluene, xylene or decalin, and halogenated hydrocarbons, such as e.g. chlorobenzene, dichlorobenzene, dichloromethane, chloroform, tetrachloromethane, dichloroethane or trichloroethane, ethers, such as diethyl ether, diisopropyl ether, methyl tert-butyl ether, methyl tert-amyl ether, dioxane, tetra-hydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-di-methylacetamide, N-methylformanilide, N-methylpyrrolidone or hexamethylphosphortriamide; sulphoxides, such as dimethyl sulphoxide or sulphones, such as sulpholane. Particular preference is given to using methylene chloride, dichloroethane, toluene, chlorobenzene, methyl tert-butyl ether or THF.

The reaction mixture is worked-up in an anhydrous manner by freeing the mixture from salts (filtration) and removing the solvents in vacuo. Aqueous work-up is also possible. It is also possible to further react the mixture without prior isolation.

The purity of the compounds of the formula (I) is very high and is in the region of 95-97%, which can be used further without purification step. In particular, the reaction according to the invention is characterized by the use of favourable raw materials, and also by process control that can be carried out particularly well and easily even on an industrial scale.

The compounds of the formula (I) according to the invention are valuable intermediates in the synthesis of pyrazoles, which are important building blocks for producing insecticidally effective anthranilamides (WO2007/112893, WO2007/144100) and can be further reacted e.g. in accordance with scheme (I) below. For example, the following compounds can be obtained through the further reaction of the compounds of the formula (I) according to scheme (I):

methyl 1-(3-chloropyridin-2-yl)-5-hydroxy-3-(hydroxymethyl)-4,5-dihydro-1H-pyrazole-5-carboxylate (cf. preparation example No. 6); ethyl 1-(3-chloropyridin-2-yl)-5-hydroxy-3-(hydroxymethyl)-4,5-dihydro-1H-pyrazole-5-carboxylate (preparation example No. 7); methyl 1-(3-chloropyridin-2-yl)-3-{[(methylsulphonyl)oxy]methyl}-1H-pyrazole-5-carboxylate (preparation example No. 8); methyl 3-(chloromethyl)-1-(3-chloropyridin-2-yl)-1H-pyrazole-5-carboxylate (preparation example No. 9).

Scheme (I)

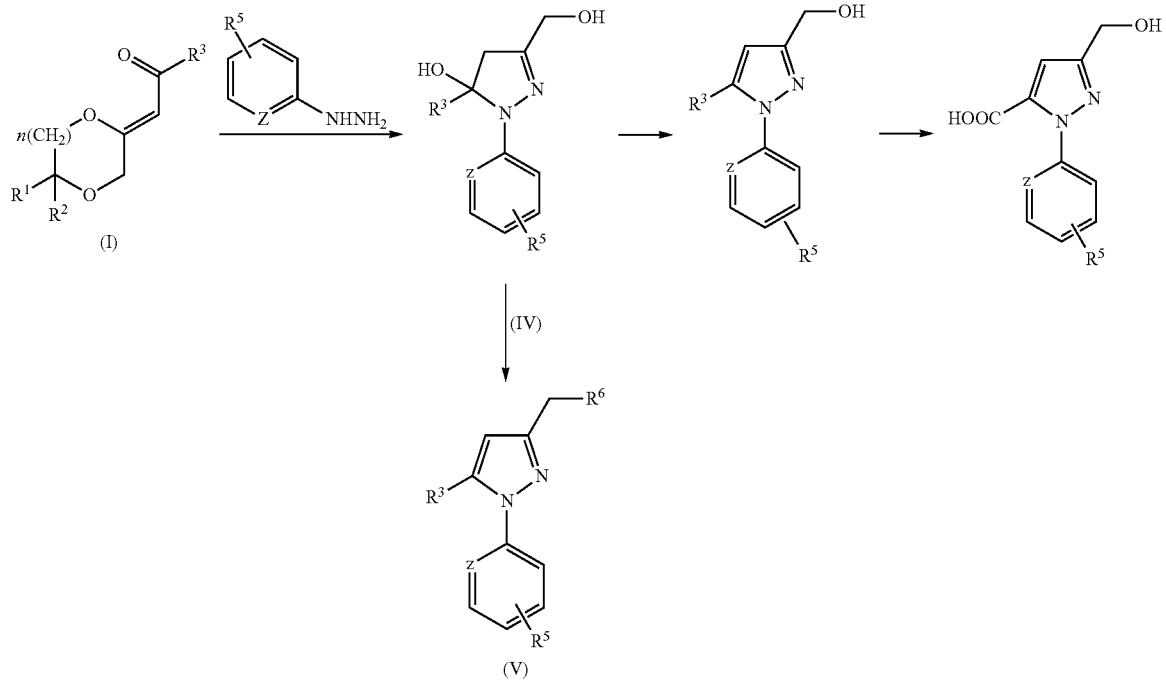

where
$R^1$, $R^2$, $R^3$ and n have the meanings given above,
$R^5$ is halogen, cyano, nitro, alkyl, cycloalkyl, haloalkyl, halocycloalkyl, alkoxy, haloalkoxy, alkylamino, dialkylamino, cycloalkylamino,
$R^6$ is halogen, $OSO_2Me$, $O(C=O)CH_3$,
Z is CH, N.

PREPARATION EXAMPLES

The following preparation examples illustrate the invention without limiting it. In particular, preparation Examples 1A, 1 to 4 and 5 show the preparation of compounds of the formula (I) by the process according to the invention, preparation Examples 6 to 9 and Example 10 demonstrate the use of the compounds of the formula (I) as intermediates for the further reaction to pyrazoles, which are important building blocks in the synthesis of insecticidally effective anthranilamides.

Example 1A

Methyl (3E)-3-(2,2-dimethyl-1,3-dioxolan-4-ylidene)-2-oxopropanoate

The solution of methyloxalyl chloride (122 g, 1 mol) in 100 ml of $CH_2Cl_2$ was added at 0° C. to the solution of 2,2-dimethyl-4-methylene-1,3-dioxolane (114 g, 1 mol) and pyridine (79 g, 1 mol) in 200 ml of $CH_2Cl$. The reaction mixture was after-stirred for 1 hour at 20° C. and diluted with 500 ml of water. The organic phase was separated off and dried with $MgSO_4$, and $CH_2Cl_2$ was removed in vacuo. Yield 180 g (90%).

M.p. 61-63° C.

$^1H$ NMR ($CDCl_3$) δ: 6.88 (1H, s), 5.10 (2H, s), 3.8 (3H, s), 1.5 (6H, s);

Example 1B

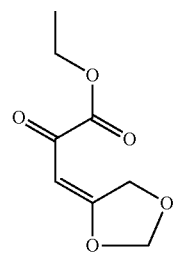

(E)-Ethyl 3-(1,3-dioxolan-4-ylidene)-2-oxopropanoate

The solution of ethyloxalyl chloride (10.3 g, 75.5 mmol) in $CH_2Cl_2$ (10 mL) was added at 0° C. to the solution of methylene dioxolane (6.5 g, 75.5 mmol) and pyridine (6.3 g, 80 mmol) in CH$_2$Cl (80 mL). The reaction mixture was stirred for 10 hours at 5° C. and diluted with 200 ml of water. The product was extracted with 200 ml of hexane, the solution of hexane was dried with MgSO$_4$ and concentrated by evaporation. This gave 11.9 g (85%) of the product, b.p. 106-110° C./0.5 mmHg.

$^1$H NMR (CDCl$_3$) δ: 6.60 (1H, s, CH), 5.45 (2H, s, CH$_2$O), 5.01 (2H, s, CH$_2$O), 4.33 (2H, q, OCH$_2$), 1.38 (3H, t, CH$_3$).

Example 1

(E)-3-(1,3-dioxolan-4-ylidene)-1,1,1-trifluoropropan-2-one

The solution of trichloroacetic anhydride (39.3 g, 187 mmol) in 30 ml of CH$_2$Cl$_2$ was added dropwise at 0° C. to the solution of 4-methylene-1,3-dioxolane (16.1 g, 187 mmol) and pyridine (16.3 g, 15.3 ml, 205 mmol) in 150 ml of CH$_2$Cl$_2$. The reaction mixture was stirred for 20 hours at 5° C. and diluted with 100 ml of water. The product was extracted with toluene, the organic phase was dried with MgSO$_4$ and toluene was removed in vacuo. The product was purified by distillation. Yield of (E)-3-(1,3-dioxolan-4-ylidene)-1,1,1-trifluoropropan-2-one is 28.3 g (83%), b.p.: 83-85° C./15 mbar.

Analytical Characterization
$^1$H NMR (CDCl$_3$) δ: 6.16 (1H, s), 5.51 (2H, s), 5.05 (2H, s) ppm;
$^{13}$C NMR (125 MHz, CDCl$_3$) δ: 180.20 (q), 175.76, 116.29 (q), 99.15, 90.83, 71.02 ppm;
$^{19}$F NMR (CDCl$_3$) δ: −77.55 (s) ppm.

Example 2

(E)-3-(2,2-dimethyl-1,3-dioxolan-4-ylidene)-1,1,1-trifluoropropan-2-one

The procedure is as described in Example 1 but using 2,2-dimethyl-4-methylene-1,3-dioxolane instead of 4-methylene-1,3-dioxolane.

Yield (80%), b.p. 72-74° C./20 mbar.
Analytical Characterization
$^1$H NMR (CDCl$_3$) δ: 6.03 (1H, s), 5.12 (2H, s), 1.59 (6H, s);
$^{13}$C NMR (CDCl$_3$) δ: 180.09 (q), 176.76, 117.08, 116.39 (q), 90.01, 71.19, 24.86 ppm;
$^{19}$F NMR (CDCl$_3$) δ: −77.63 (s) ppm.

Example 3

(E)-1,1,1-trichloro-3-(1,3-dioxolan-4-ylidene)propan-2-one

The solution of trichloroacetyl chloride (10.0 g, 55 mol) in 20 ml of CH$_2$Cl$_2$ was added at 0° C. to the solution of 4-methylene-1,3-dioxolane (4.7 g, 55 mmol) and pyridine (4.8 g, 4.5 ml, 60 mmol). The reaction mixture was after-stirred for 4 hours at 20° C. and diluted with 100 ml of water. The product was extracted with hexane, the organic phase was dried with MgSO$_4$ and hexane was removed in vacuo. The product was purified by crystallization from hexane.

Yield of (E)-1,1,1-trichloro-3-(1,3-dioxolan-4-ylidene) propan-2-one 7.5 g (59%).
M.p. 64° C.
Analytical Characterization
$^1$H NMR (CDCl$_3$) δ: 6.38 (1H, br. s), 5.46 (2H, s), 5.02 (2H, s) ppm;
$^{13}$C NMR (CDCl$_3$) δ: 181.45, 174.71, 98.92, 96.50, 89.87, 70.55 ppm.

Example 4

(E)-1,1,1-trichloro-3-(2,2-dimethyl-1,3-dioxolan-4-ylidene)propan-2-one

The procedure is as described in Example 3 but using 2,2-dimethyl-4-methylene-1,3-dioxolane instead of 4-methylene-1,3-dioxolane.

Yield of 1,1,1-trichloro-3-(2,2-dimethyl-1,3-dioxolan-4-ylidene)propan-2-one:
(72%), b.p. 140° C./0.5 mbar, m.p. 40-42° C.
Analytical Characterization:
$^1$H NMR (CDCl$_3$) δ: 6.28 (1H, br. t), 5.12 (2H, br. d), 1.59 (6H, s) ppm;
$^{13}$C NMR (CDCl$_3$) δ: 181.25, 175.24, 116.15, 96.16, 88.97, 70.60, 25.05 ppm.

Example 5

Ethyl (3E)-3-(2,2-dimethyl-1,3-dioxolan-4-ylidene)-2-oxopropanoate

The procedure is as described in Example 4, but using ethyl chloro(oxo)acetate instead of trichloroacetyl chloride. Yield 85%, oil.

Analytical Characterization:
$^1$H NMR (CDCl$_3$) δ: 6.28 (1H, br. t), 5.12 (2H, br. d), 1.59 (6H, s) ppm;
$^{13}$C NMR (CDCl$_3$) δ: 181.25, 175.24, 116.15, 96.16, 88.97, 70.60, 25.05 ppm.

Example 6

Methyl 1-(3-chloropyridin-2-yl)-5-hydroxy-3-(hydroxymethyl)-4,5-dihydro-1H-pyrazole-5-carboxylate The mixture of methyl (3E)-3-(2,2-dimethyl-1,3-dioxolan-4-ylidene)-2-oxopropanoate (20 g, 0.1 mol) and 2-hydrazino-3-chloropyridine (21.4 g, 0.15 mol) in 150 ml of isopropanol was stirred for 8 hours at RT. The precipitate was filtered off and washed with hexane. This gave 27.6 g (85%) of the product as a pale yellow solid with a m.p. of 113-115° C.

$^1$H NMR (DMSO d$_6$) δ: 7.99 (1H, d); 7.65 (1H, d); 6.85 (1H, dd); 6.4 (1H, bs); 4.51 (2H, br. s); 3.25 (1H, d); 3.05 (1H, d), 2.55 (s, 1H) ppm.

Example 7

Ethyl 1-(3-chloropyridin-2-yl)-5-hydroxy-3-(hydroxymethyl)-4,5-dihydro-1H-pyrazole-5-carboxylate The mixture of ethyl (3E)-3-(2,2-dimethyl-1,3-dioxolan-4-ylidene)-2-oxopropanoate (21.4 g, 0.1 mol) and 2-hydrazino-3-chloropyridine (21.4 g, 0.15 mol) in 150 ml of ethanol was stirred for 8 hours at RT. Ethanol was removed in vacuo and the residue was taken up in 200 ml of methyl tert-butyl ethyl. The organic phase was washed three times with in each case 50 ml of 1% HCl and concentrated by evaporation. This gave 36 g (86% yield) of the product as a viscous oil with a purity (HPLC) of 97%.

Analytical Characterization
$^1$H NMR (DMSO d$_6$) δ: 7.99 (1H, d); 7.65 (1 h, d); 6.85 (1H, dd); 6.0 (OH, bs); 4.51 (2H, br. s); 4.25 (2H, q); 3.25 (1H, d); 3.05 (1H, d), 1,28 (t, 3H) ppm.

Example 8

Methyl 1-(3-chloropyridin-2-yl)-3-{[(methylsulphonyl)oxy]methyl}-1H-pyrazole-5-carboxylate Methyl 1-(3-chloropyridin-2-yl)-5-hydroxy-3-(hydroxymethyl)-4,5-dihydro-1H-pyrazole-5-carboxylate (28.5 g, 0.1 mol) and 15 g of triethylamine were introduced as initial charge in 150 ml of THF and the solution was cooled to 5° C. At 0-5° C., 11.4 g of mesylene chloride were added over the course of 20 min and the mixture was after-stirred for 2 hours at 0° C. The reaction mixture was diluted with water and the product was extracted with ethyl acetate. The solution was washed, dried and concentrated by evaporation. The viscous oily residue 31 g comprised, according to LC/MS, 98% of the product with m/e 345.

Example 9

Methyl 3-(chloromethyl)-1-(3-chloropyridin-2-yl)-1H-pyrazole-5-carboxylate

Methyl 1-(3-chloropyridin-2-yl)-5-hydroxy-3-(hydroxymethyl)-4,5-dihydro-1H-pyrazole-5-carboxylate (28.5 g, 0.1 mol) was dissolved in 100 ml of $CH_2Cl_2$ and the solution was cooled to 5° C. $SOCl_2$ (0.12 mol) in 30 ml of $CH_2Cl_2$ was slowly added dropwise at this temperature. The mixture was after-stirred for 4 hours at RT and concentrated by evaporation in vacuo. The product was purified by column chromatography on $SiO_2$ (eluent hexane/ethyl acetate). Oil.
Analytical Characterization
$^1$H NMR ($CD_3CN$) δ: 8.52 (1H, d); 8.06 (1H, d), 7.55 (1H, dd); 7.10 (1H, s); 4.75 (2H, s); 3.75 (3H, s) ppm.

Example 10

Methyl 1-(3-chloropyridin-2-yl)-3-(hydroxymethyl)-1H-pyrazole-5-carboxylate

HCl solution (9.1 g, as 4% solution in methanol) was added to the suspension of 28.5 g (0.1 mol) of methyl 1-(3-chloropyridin-2-yl)-5-hydroxy-3-(hydroxymethyl)-4,5-dihydro-1H-pyrazole-5-carboxylate in 100 ml of methanol. After ca. 30 min at 25-30° C., a clear, yellow solution had formed. Methanol was removed in vacuo and the precipitate was washed with water. Yield 26.7 g, 100%. M.p. 104° C.
Analytical Characterization
$^1$H NMR (DMSO $d_6$) δ: 8.52 (1H, d); 8.06 (1H, d), 7.55 (1H, dd); 7.10 (1H, s); 5.4 (1H, b.s) 4.5 (2H, s); 3.75 (3H, s) ppm.

The invention claimed is:

1. A compound of general formula (I)

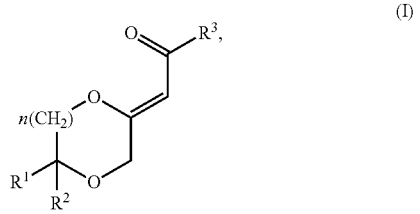

in which
$R^1$ and $R^2$, independently of one another, are hydrogen, alkyl, haloalkyl, aryl or alkylaryl,
n is 0 or 1,
$R^3$ is $CX_3$, (C=O)Oalkyl or (C=O)Oaryl, and
X is halogen.

2. The compound according to claim 1, wherein
$R^1$ and $R^2$, independently of one another, are hydrogen or methyl,
n is 0,
$R^3$ is $CX_3$ or (C=O)Oalkyl, and
X is chlorine.

3. The compound according to claim 1, wherein
$R^1$ and $R^2$, independently of one another, are hydrogen or methyl,
n is 0, and
$R^3$ is (C=O)Omethyl.

4. A process for preparing a compound of formula (I) according to claim 1, comprising, reacting a compound of formula (II),

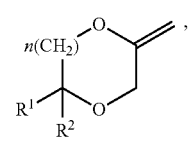

in which
$R^1$ and $R^2$, independently of one another, are hydrogen, alkyl, haloalkyl, aryl or alkylaryl, and
n is 0 or 1,
with a compound of general formula (III),

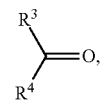

in which
$R^3$ is $CX_3$, (C=O)Oalkyl or (C=O)Oaryl,
X is halogen, and
$R^4$ is X, O(C=O)$R^3$ or $(CH_3)_3$COO,
to give a compound of the general formula (I).

5. The process of claim 4, wherein $R^4$ is X.

6. The process of claim 4, further comprising carrying out said process in a temperature range from −20° C. to 100° C.

7. The process of claim 4, wherein 1 mol of said compound of the formula (II) is reacted with 0.8 to 1.5 mol of said compound of the formula (III).

8. A process for the preparation of a compound of Formula (V):

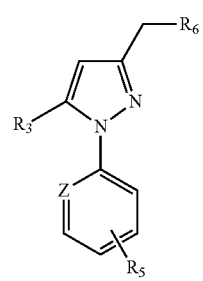

wherein
$R^3$ is $CX_3$, (C=O)Oalkyl, or (C=O)Oaryl;
$R^5$ is halogen, cyano, nitro, alkyl, cycloalkyl, haloalkyl, halocycloalkyl, alkoxy, haloalkoxy, alkylamino, dialkylamino, or cycloalkylamino;
$R^6$ is halogen, $OSO_2Me$, or O(C=O)$CH_3$, and
Z is CH or N;

comprising, reacting a compound of Formula (I):

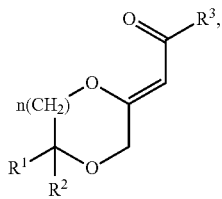

wherein $R^1$ and $R^2$, independently of one another, are hydrogen, alkyl, haloalkyl, aryl, or alkylaryl;

n is 0 or 1; and $R^3$ is $CX_3$, (C=O)Oalkyl, or (C=O)Oaryl;

with a compound of the formula:

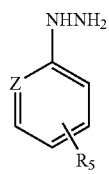

wherein $R^5$ and Z have the meaning given above.

to give a compound of Formula (V).

9. The compound of claim 1, wherein the compound of formula (I) is selected from the group consisting of:

1,1,1-Trichloro-3-(2,2,-dimethyl-1,3-dioxolan-4-ylidene) acetone;

Methyl 3-(2,2-dimethyl-1,3-dioxolan-4-ylidene)-2-oxopropanoate;

Methyl 3-(1,3-dioxolan-4-ylidene)-2-oxopropanoate;

Ethyl 3-(2,2-dimethyl-1,3-dioxolan-4-ylidene)-2-oxopropanoate; and

Ethyl 3-(5,5-dimethyl-1,4-dioxan-2-ylidene)-2-oxopropanoate.

10. The process of claim 8, wherein the compound of Formula (V) is selected from the group consisting of:

Methyl 1-(3-chloropyridin-2-yl)-5-hydroxy-3-(hydroxymethyl)-4,5-dihydro-1H-pyrazole-5-carboxylate;

Ethyl 1-(3-chloropyridin-2-yl)-5-hydroxy-3-(hydroxymethyl)-4,5-dihydro-1H-pyrazole-5-carboxylate;

Methyl 1-(3-chloropyridin-2-yl)-3-{[(methylsulphonyl)oxy]methyl}-1H-pyrazole-5-carboxylate; and Methyl 3-(chloromethyl)-1-(3-chloropyridin-2-yl)-1H-pyrazole-5-carboxylate.

* * * * *